(12) United States Patent
Walsh et al.

(10) Patent No.: US 7,935,299 B2
(45) Date of Patent: *May 3, 2011

(54) METHOD AND APPARATUS FOR FORMING A BATT OF PARTICULATE MATERIAL FOR USE AS A COMPONENT IN AN ABSORBENT CORE ASSEMBLY

(75) Inventors: Bradley Edward Walsh, Cincinnati, OH (US); Horst Blessing, Cincinnati, OH (US); Darrell Ian Brown, Mason, OH (US); John Glasgow Burns, Jr., Springfield, OH (US); Joseph Allen Eckstein, Sunman, IN (US); Volker Maier, Euskirchen (DE)

(73) Assignee: The Procter & Gamble Company, Cincinnati, OH (US)

( * ) Notice: Subject to any disclaimer, the term of this patent is extended or adjusted under 35 U.S.C. 154(b) by 4 days.

This patent is subject to a terminal disclaimer.

(21) Appl. No.: 12/337,713

(22) Filed: Dec. 18, 2008

(65) Prior Publication Data
US 2009/0098285 A1 Apr. 16, 2009

Related U.S. Application Data

(63) Continuation of application No. 11/206,004, filed on Aug. 17, 2005, now Pat. No. 7,524,449.

(51) Int. Cl.
*B27N 3/04* (2006.01)
*A61F 13/15* (2006.01)

(52) U.S. Cl. ....... 264/511; 264/517; 264/112; 425/80.1; 425/81.1

(58) Field of Classification Search ........................ None
See application file for complete search history.

(56) References Cited

U.S. PATENT DOCUMENTS

| | | | |
|---|---|---|---|
| 3,882,216 | A | 5/1975 | Delanty et al. |
| 4,761,258 | A | 8/1988 | Enloe |
| 4,940,464 | A | 7/1990 | Van Gompel et al. |
| 4,994,053 | A | 2/1991 | Lang |
| 5,092,861 | A | 3/1992 | Nomura et al. |
| 5,246,433 | A | 9/1993 | Hasse et al. |

(Continued)

FOREIGN PATENT DOCUMENTS
CA  2 051 149 C  2/2002
(Continued)

OTHER PUBLICATIONS

International Search Report & Written Opinion, dated Jan. 23, 2007, PCT/IB2006/052734, 11 pgs.

*Primary Examiner* — Mary Lynn F Theisen
(74) *Attorney, Agent, or Firm* — Laura L. Whitmer; Amy M. Foust (57) ABSTRACT

A method and apparatus for forming a wad of particulate material which may be used in an absorbent article. The apparatus may include a laydown drum having a plurality of vacuum zones, a plurality of fence zones, and a plurality of blow-off zones. The plurality of vacuum zones may be substantially permeable to permit vacuum air to pass through and into the laydown drum. The plurality of fence zones may be substantially impermeable to inhibit air to pass through. The plurality of blow-off zones may be substantially permeable to permit blown air to pass out of and through said laydown drum. The apparatus may also include a deposition chute for depositing particulate material on a web of material in close proximity to the laydown drum. A shield may also be attached to the deposition chute.

7 Claims, 7 Drawing Sheets

U.S. PATENT DOCUMENTS

| | | |
|---|---|---|
| 5,494,622 A | 2/1996 | Heath et al. |
| 5,569,234 A | 10/1996 | Buell et al. |
| 5,897,545 A | 4/1999 | Kline et al. |
| 5,957,908 A | 9/1999 | Kline et al. |
| 6,120,487 A | 9/2000 | Ashton |
| 6,120,489 A | 9/2000 | Johnson et al. |
| 6,706,129 B2 | 3/2004 | Ando et al. |
| 7,297,307 B2 | 11/2007 | Yasumura et al. |
| 2002/0056516 A1 | 5/2002 | Ochi |
| 2002/0156441 A1 | 10/2002 | Sawyer et al. |
| 2002/0188266 A1 | 12/2002 | Kling et al. |
| 2003/0132556 A1 | 7/2003 | Venturino et al. |
| 2003/0139721 A1 | 7/2003 | Melius et al. |
| 2003/0171728 A1 | 9/2003 | Heyn et al. |
| 2003/0233082 A1 | 12/2003 | Kline et al. |
| 2006/0048880 A1 | 3/2006 | Blessing et al. |

FOREIGN PATENT DOCUMENTS

| | | |
|---|---|---|
| EP | 0 292 623 A1 | 11/1988 |
| EP | 0 478 182 A1 | 1/1995 |
| EP | 0 958 801 B1 | 11/1999 |
| EP | 1 621 167 A2 | 2/2006 |
| FR | 2 521 003 B1 | 5/1987 |
| WO | WO 02/049565 A2 | 6/2002 |
| WO | WO 03/059229 A1 | 7/2003 |
| WO | WO 03/059232 A2 | 7/2003 |
| WO | WO 03/059233 A2 | 7/2003 |

METHOD AND APPARATUS FOR FORMING A BATT OF PARTICULATE MATERIAL FOR USE AS A COMPONENT IN AN ABSORBENT CORE ASSEMBLY

CROSS REFERENCE TO RELATED APPLICATION

This application is a continuation application of U.S. application Ser. No. 11/206,004, filed Aug. 17, 2005, now U.S. Pat. No. 7,524,449, which is herein incorporated by reference in its entirety.

FIELD OF THE INVENTION

The present invention relates to a method and apparatus for forming a batt of particulate material for use as a component in an absorbent core assembly. Further, the present invention relates to a method and apparatus for forming a batt of fluff material and superabsorbent polymer for use as a component in an absorbent core assembly.

BACKGROUND OF THE INVENTION

Absorbent articles having absorbent core assemblies for use in absorbing body fluids are well known in the art. For example, disposable diapers are often constructed having an absorbent core assembly positioned between layers of materials. Said absorbent core assemblies often comprise a mixture of particulate materials (e.g., fluff material and superabsorbent polymer) which are formed into a batt or wad. Said batt or wad may be positioned between two or more layers of materials. One such layer may be adapted to face the wearer's body, such as a dusting layer. Another such layer conveniently may be adapted to face away from the person's body, such as a core wrap. Said batt is intended to extended longitudinally inboard of the end edges of the diaper (i.e., batt does not extend entire length of diaper).

In the manufacturing of said absorbent core assemblies, a variety of techniques are well known. For example, discrete batts may be discretely formed by the use of vacuum zones within a laydown drum. However, such current techniques and apparatus experience problems with superabsorbent polymer being inadvertently deposited substantially along the entire length of the diaper. Said problem presents issues with the superabsorbent polymer being free from the fluff material and subsequently pierce through the topsheet causing said superabsorbent polymer to be deposited on the wearer's skin which is a consumer negative aesthetically. Additionally, another problem may exist when fluff material is inadvertently deposited substantially along the entire length of the diaper thus interfering with an end seal necessary to contain the absorbent core assembly.

What is needed is a method and apparatus for forming a batt of particulate material (e.g., fluff material and superabsorbent polymer) for use as a component in an absorbent core assembly.

SUMMARY OF THE INVENTION

A method of forming a wad of particulate material (e.g., superabsorbent polymer and fluff material) which may be used in an absorbent article. The method may include the step of providing a laydown drum. The laydown drum may have a plurality of vacuum zones. These vacuum zones may be substantially permeable to permit vacuum air to pass through and into the laydown drum. The laydown drum may also include a plurality of fence zones. These fence zones may be substantially impermeable to inhibit air to pass through. The laydown drum may also include a plurality of blow-off zones. These blow-off zones may be substantially permeable to permit blown air to pass out of and through the laydown drum. The method may also include the step of providing a first web of material and positioning the first web of material substantially adjacent to the laydown drum. The method may also include the step of generating a vacuum through the laydown drum and the first web of material such that vacuum air is passed through said vacuum zones. The method may also include the step of depositing superabsorbent polymer and fluff material onto the first web of material such that the vacuum being pulled through the vacuum zones is used to form a wad. The method may also include the step of blowing air through the blow-off zones so as to substantially displace the superabsorbent polymer and the fluff material from a position located above the blow-off zones. The method may also include the step of providing a second web of material and positioning the second web of material adjacent the superabsorbent polymer and the fluff material. The method may also include the step of combining the second web of material to the first web of material. The method may also include the step of severing the webs to form a plurality of wads. The combining step may include adhesive bonding of the first and second webs of materials. The adhesive bonding may be intermittently applied between discrete wads. The combining step may also include mechanical bonding of the first and second webs of materials. The mechanical bonding may be intermittently applied between discrete wads. The method may also include the step of shielding of the deposited superabsorbent polymer.

An apparatus for forming a wad of particulate material (e.g., superabsorbent polymer and fluff material) which may be used in an absorbent article. The apparatus may include a laydown drum. The laydown drum may include a plurality of vacuum zones. These vacuum zones may be substantially permeable to permit vacuum air to pass through and into the laydown drum. The laydown drum may also include a plurality of fence zones. These fence zones may be substantially impermeable to inhibit air to pass through. The laydown drum may also include a plurality of blow-off zones. These blow-off zones may be substantially permeable to permit blown air to pass out of and through the laydown drum. The apparatus may also include a deposition chute for depositing superabsorbent polymer and fluff material. The chute may be in close proximity to the laydown drum. The apparatus may also include a shield attached to said deposition chute. The shield may be adapted to deflect superabsorbent polymer.

Various additional features, advantages and objectives of the invention will become more readily apparent to those of ordinary skill in the art upon review of the following detailed description of the preferred embodiments taken in conjunction with the accompanying drawings.

BRIEF DESCRIPTION OF THE DRAWINGS

FIG. 2a shows the absorbent core assembly from that of FIG. 1a;

DETAILED DESCRIPTION OF THE EMBODIMENTS

Various definitions of terms used herein are provided as follows:

The term "absorbent article" herein refers to devices which absorb and contain body exudates and, more specifically, refers to devices which are placed against or in proximity to the body of the wearer to absorb and contain the various exudates discharged from the body, such as: incontinence briefs, incontinence undergarments, absorbent inserts, diaper holders and liners, feminine hygiene garments and the like. The absorbent article may have an absorbent core having a garment surface and a body surface; a liquid permeable topsheet positioned adjacent the body surface of the absorbent core; and a liquid impermeable backsheet positioned adjacent the garment surface of the absorbent core.

The term "disposable" is used herein to describe absorbent articles which generally are not intended to be laundered or otherwise restored or reused as absorbent articles (i.e., they are intended to be discarded after a single use and, preferably, to be recycled, composted or otherwise discarded in an environmentally compatible manner).

The term "diaper" herein refers to an absorbent article generally worn by infants and incontinent persons about the lower torso.

The term "pant", as used herein, refers to disposable garments having a waist opening and leg openings designed for infant or adult wearers. A pant may be placed in position on the wearer by inserting the wearer's legs into the leg openings and sliding the pant into position about the wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the term "pant" is used herein, pants are also commonly referred to as "closed diapers", "prefastened diapers", "pull-on diapers", "training pants" and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. patent application Ser. No. 10/171,249, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

The term "machine direction (MD)" or "longitudinal" herein refers to a direction running parallel to the maximum linear dimension of the article and/or fastening material and includes directions within ±45° of the longitudinal direction.

The term "cross direction (CD)", "lateral" or "transverse" herein refers to a direction which is orthogonal to the longitudinal direction.

The term "joined" encompasses configurations whereby an element is directly secured to another element by affixing the element directly to the other element, and configurations whereby an element is indirectly secured to another element by affixing the element to intermediate member(s) which in turn are affixed to the other element.

The term "fluff material" refers to any material suitable for suspending and/or entangling with superabsorbent polymer. Fluff material may be made of a variety of materials including, but not limited to, synthetic fibers having a length suitable for airlaying, cellulose fibers including cross-linked cellulose fibers, or the like, and combinations thereof.

The term "superabsorbent polymer" refers to a polymer having a capacity for absorbing and/or storing liquid. Superabsorbent polymer may be made of a variety of materials including, but not limited to, polyacrylic acid, sodium polyacrylate, polyacrylamide, polyacrylonitrile, polyvinyl alcohol, an additional polymer of maleic anhydride, a polyether, a condensed polymer, a polysaccharide such as starch or cellulose, a protein such as collagen, or the like, and combinations thereof. Examples of the SAP's include: a cross-linked compound of sodium polyacrylate, a graft copolymer of starch having sodium polyacrylate or a graft copolymer of cellulose having polyacrylonitrile chains.

Figure 1A:
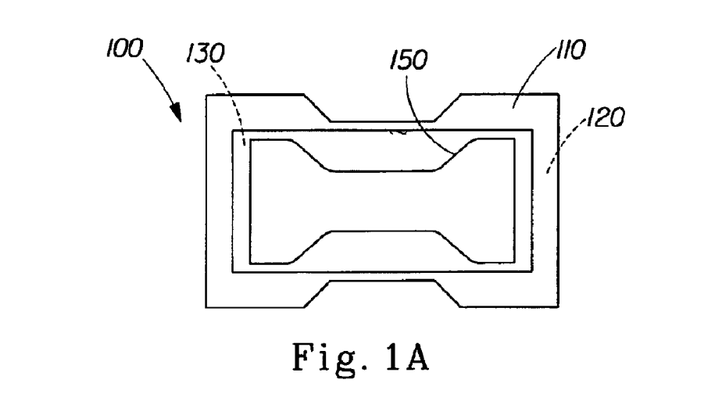
FIG. 1a shows an exemplary absorbent article in accordance with the present invention.
Figure 1B:
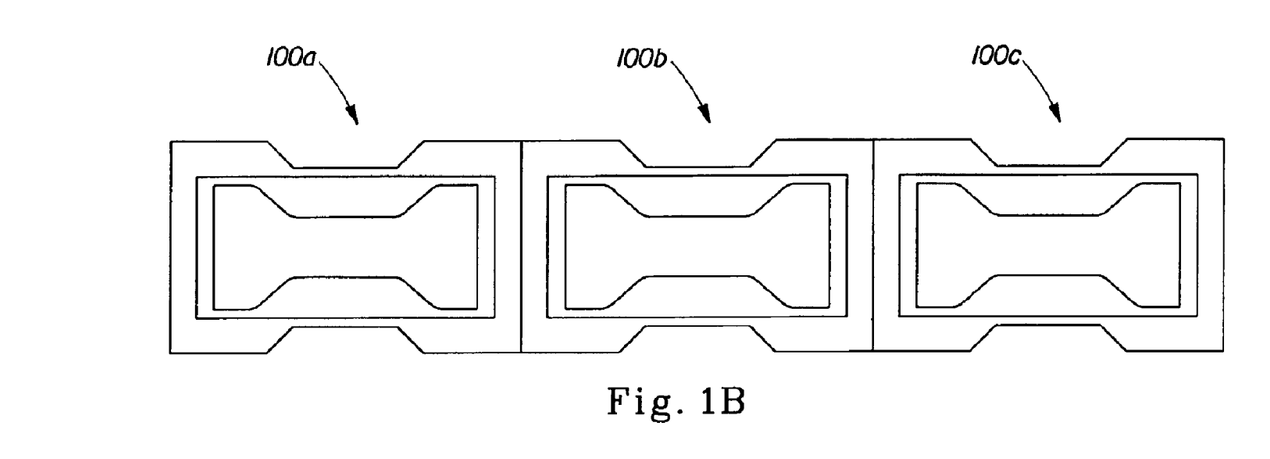
FIG. 1b shows a series of absorbent articles made from a plurality of web materials.

FIG. 1a shows an exemplary absorbent article made in accordance with the present invention. More specifically, absorbent article 100 is shown having a topsheet 110, a backsheet 120 and an absorbent core assembly 130. While other constructions of said absorbent article are well known in the art, this basic diaper construction is sufficient to articulate the benefits of the present invention. FIG. 1b shows a series of absorbent articles made from a plurality of web materials. More specifically, a first absorbent article 100a, a second absorbent article 100b and a third absorbent article 100c are shown in end-to-end configuration as would be seen prior to a final knife cut within a manufacturing process.

Figure 2A:
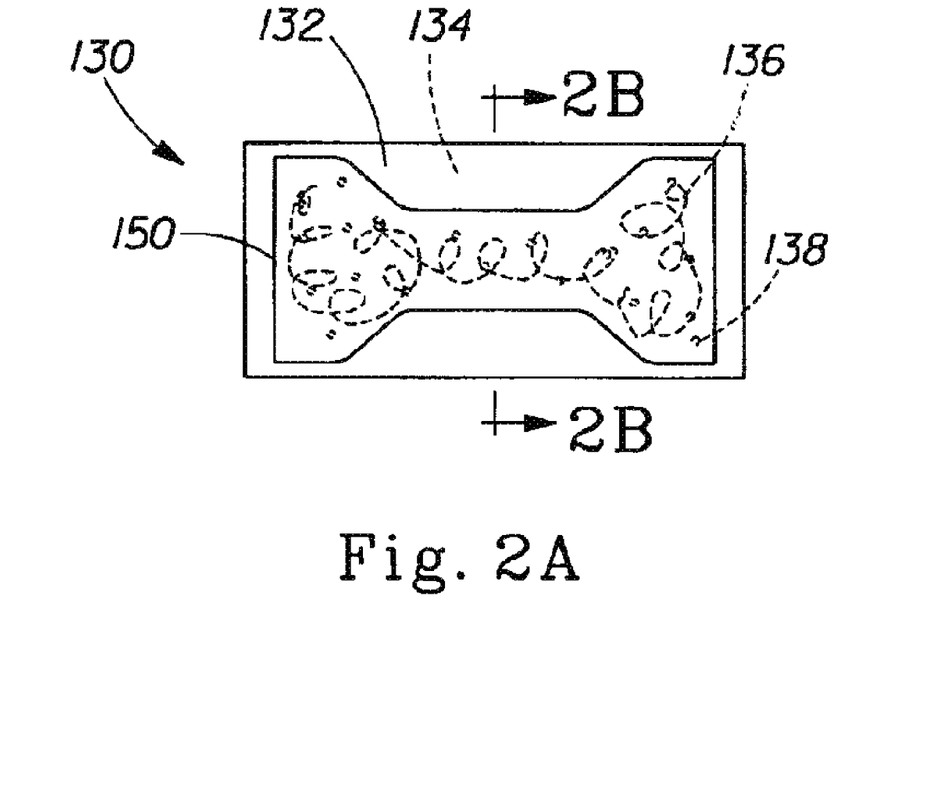
Figure 2B:
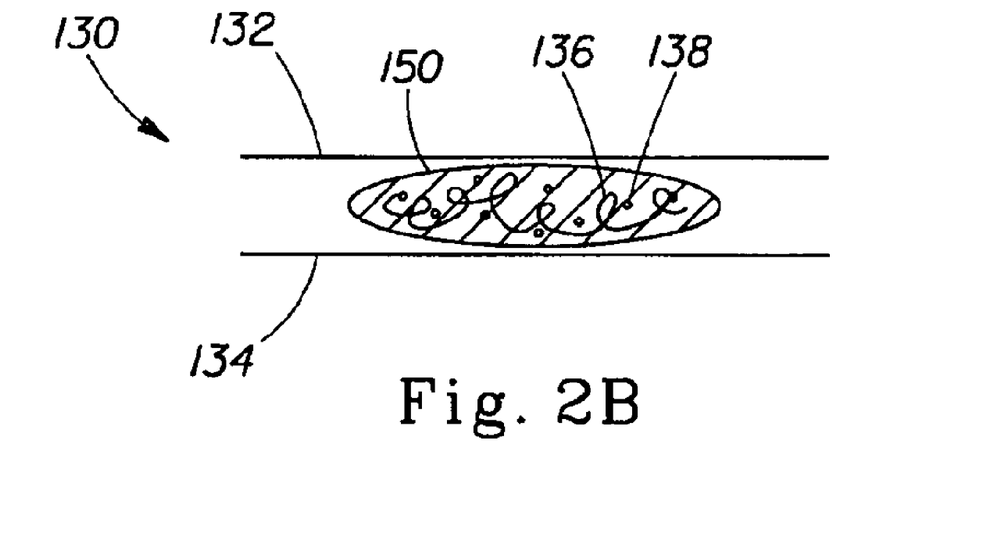
FIG. 2b shows a cross-sectional view of the absorbent core assembly from FIG. 2a taken along line A-A.

FIG. 2a shows the absorbent core assembly 130 from that of FIG. 1a. More specifically, absorbent core assembly 130 may comprise of a dusting layer 132, a core wrap layer 134, and a mixture of particulate material, for example fluff material 136 and superabsorbent polymer (hereinafter SAP) 138, positioned therebetween. FIG. 2b shows a cross-sectional view of absorbent core assembly 130 from FIG. 2a taken along line A-A. As can be appreciated from this view, the dusting layer 132 may be positioned as the top layer and core wrap layer 134 and may be positioned as the bottom layer; however, one skilled in the art would appreciate that a variety of other configurations are possible.

Figure 3:
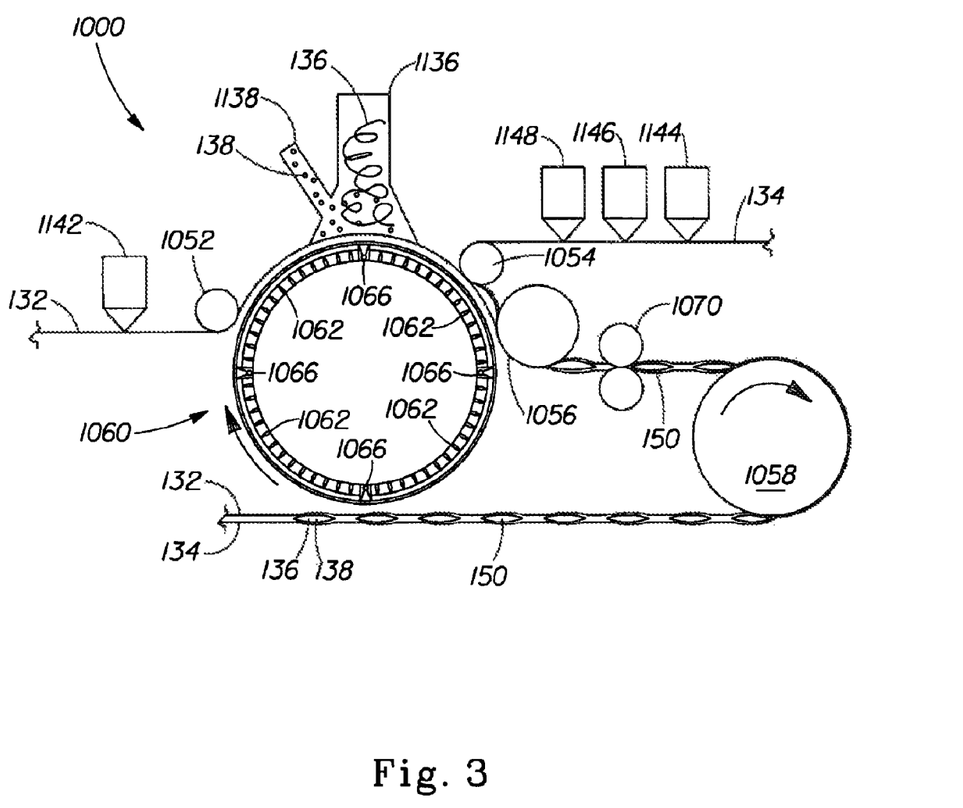
FIG. 3 shows an exemplary manufacturing process in accordance with the present invention.

FIG. 3 shows an exemplary manufacturing process in accordance with the present invention. More specifically, process 1000 is shown having a laydown drum 1060, an SAP applicator 1138, an fluff material deposition chute 1136 and a variety of other web handling devices. In this particular example, a web of dusting layer material 132 is shown being fed into said process. As shown, a central adhesive applicator 1142 may apply adhesive to at least one side of said dusting layer. While a variety of adhesive application patterns may be used, one such pattern is described later in FIG. 6a. After said central adhesive is applied, the dusting layer 132 may be fed to an underneath position in relationship to said fluff material deposition chute 1136. In doing, and throughout this manufacturing process, a variety of web handling devices may be used including, but not limited to, idlers 1052, 1054, 1056, 1058. Next, SAP 138 and fluff material 136 may be applied to the top of dusting layer 132 with the aid of vacuum being drawn through and into the interior of laydown drum 1060. Said laydown drum 1060 may comprise of multiple zones, such as vacuum zones 1062 and blow-off zones 1066. Said laydown drum 1060 is described in additional detail in FIG. 4.

In parallel with said processes, a web of core wrap material 134 may also be fed into said process in a direction relatively towards said fluff material deposition chute 1136. Further, adhesive may be applied to said core wrap as exampled by side adhesive applicator 1144, end adhesive applicator 1146 and auxiliary adhesive applicator 1148. While a variety of adhesive application patterns may be used, one such collection of patterns is described later in FIG. 6c. After said adhesive is applied, said core wrap material may be brought into contact with the dusting layer and mixture of SAP/fluff material. Next, said web of materials may be bonded. For example, a phased bonding roll 1070 may be used to provide intermittent bonding so as to bond the layer of materials in-between the discrete depositions of SAP/fluff material.

Figure 4:
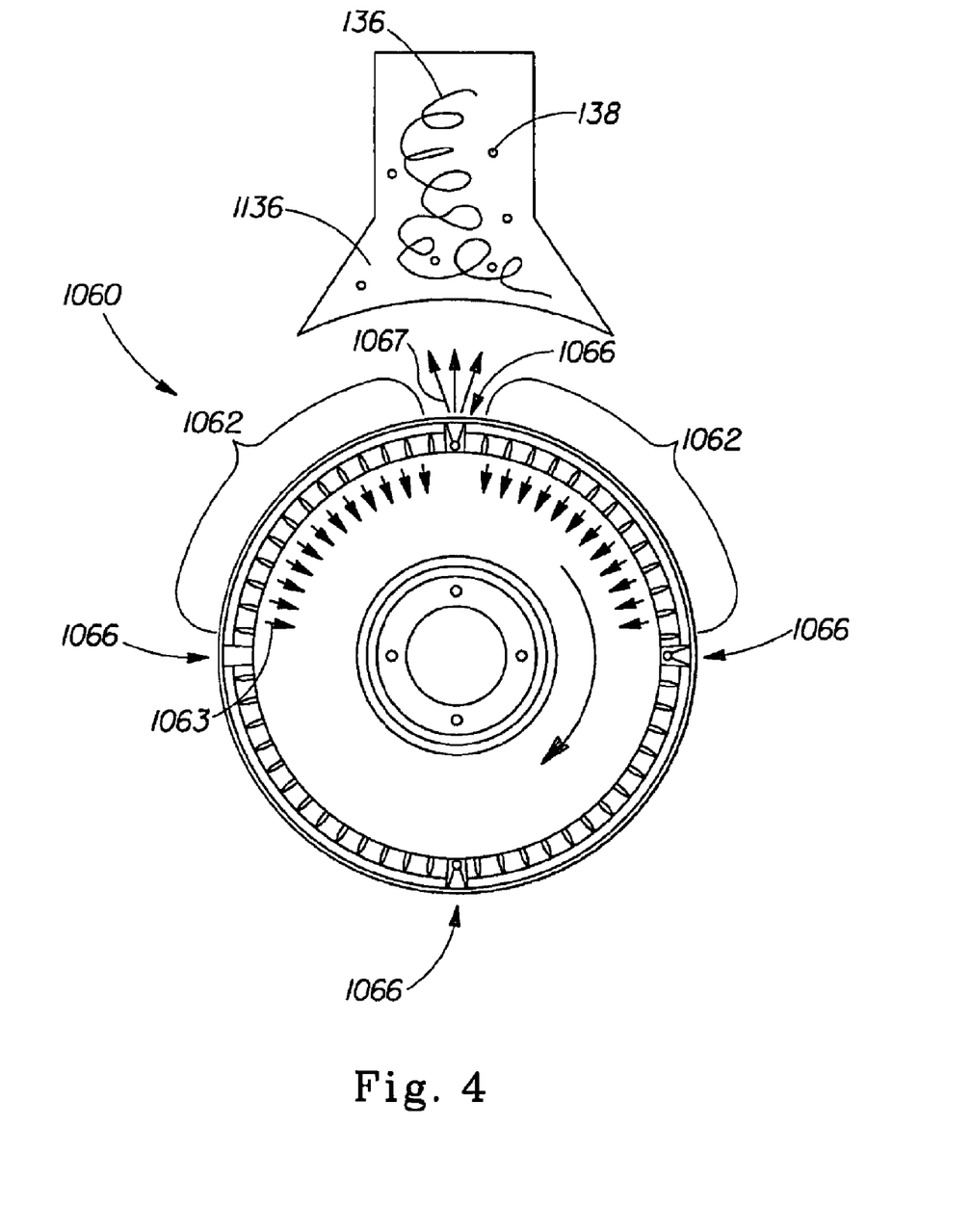
FIG. 4 shows a cross-sectional view of the laydown drum from that of FIG. 3.

FIG. 4 shows a cross-sectional view of said laydown drum 1060 from that of FIG. 3. More specifically, laydown drum 1060 is shown having at least two distinct zones, namely, a plurality of vacuum zones 1062 and a plurality of blow-off zones 1066. Also shown in this figure is fluff material deposition chute 1136 wherein SAP 138 and fluff material 136 are dispersed and mixed in air. Additionally, it is from fluff material deposition chute 1136 that SAP 138 and fluff material 136 is deposited. By way of pulling vacuum air 1063 through vacuum zones 1062, the air/particulate dispersion is directed to said vacuum zones whereupon SAP and fluff material are positioned to form a plurality of discrete wads of absorbent core material. With the additional use of blown air 1067 through blow-off zones 1066, the formation of discrete wads is improved such that the amount of loose particles of SAP and/or fluff material inadvertently positioned within the space between said wads is minimized.

Figure 5:
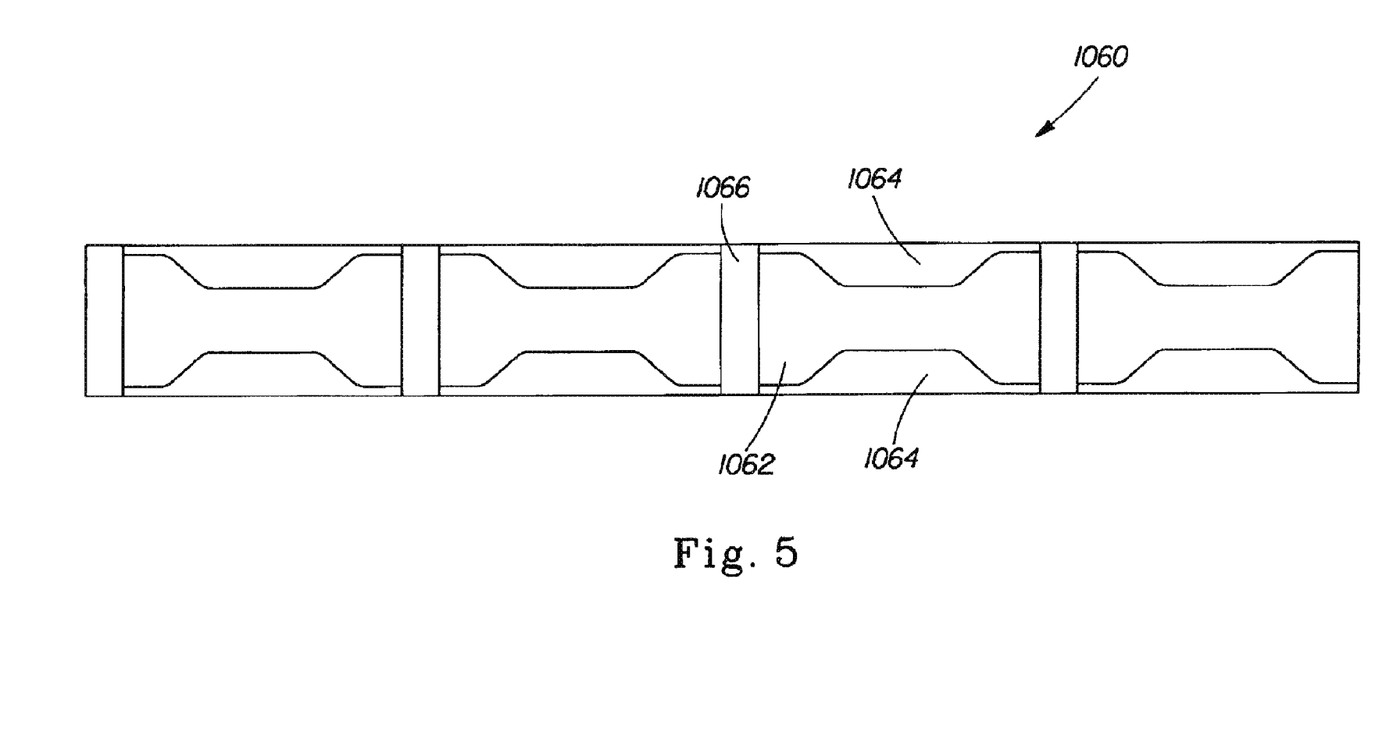
FIG. 5 shows a laid-out view of the surface of laydown drum 1060 from FIG. 4.

FIG. 5 shows a laid-out view of the surface of laydown drum 1060 from FIG. 4. As can be seen from this exemplary embodiment, vacuum zones 1062 are shaped similar to the desired outline of the discrete wads. Vacuum zones 1062 may be substantially air-permeable to allow vacuum to pass through. In addition, fence zones 1064 may be used to inhibit vacuum flow and thus inhibit the placement of SAP/fluff material in these locations. Fence zones 1064 may be substantially air-impermeable to inhibit vacuum to pass through. Further, it may be desirable to position said fence zones laterally adjacent said vacuum zones as shown in FIG. 5. Lastly, blow-off zones 1066 may be used to not only inhibit vacuum flow and thus limit the placement of SAP/fluff material in these locations, but also provide a permeable area for blown air to pass through and thus blow away any inadvertently positioned SAP/fluff material. The use of blow-off zones 1066 in the area in-between said vacuum zones provides the unique benefit of minimizing the amount of deposited SAP/fluff material which would ultimately be positioned within the waste region of the resulting absorbent article. Having SAP positioned in the waist region is often undesirable, for example, because the SAP particles are not contained by fluff material therein, thus said SAP particles are capable of piercing the top sheet and coming in harsh contact with the wearer. Such benefits would not otherwise be appreciated with the mere use of fence zones in these locations.

Figure 6:
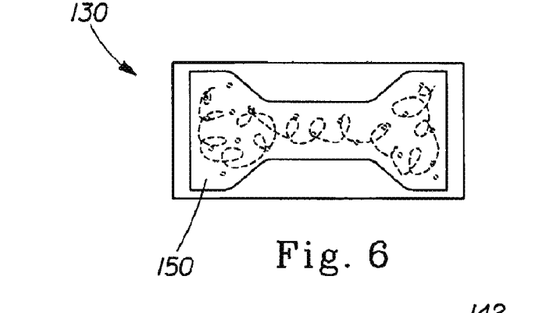
FIG. 6 shows the absorbent core assembly of FIG. 2a and further represents a compiled views of the exploded views 6a, 6b, 6c.
Figure 6A:
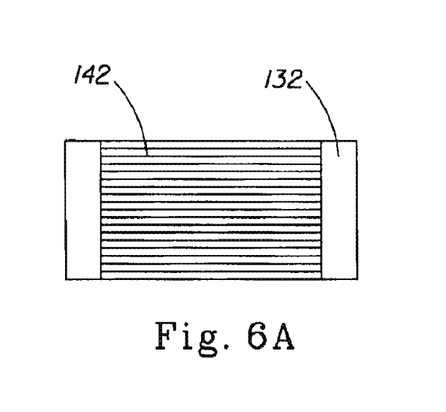
FIG. 6a shows the dusting layer having a central adhesive applied in a striped pattern from that of FIG. 6.
Figure 6B:
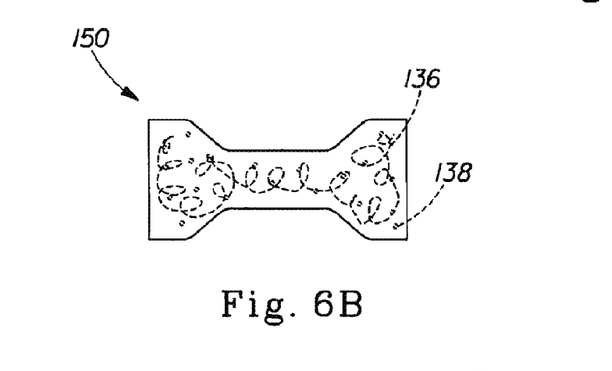
FIG. 6b shows the vacuum-formed outline of a mixture of fluff material and SAP from that of FIG. 6.
Figure 6C:
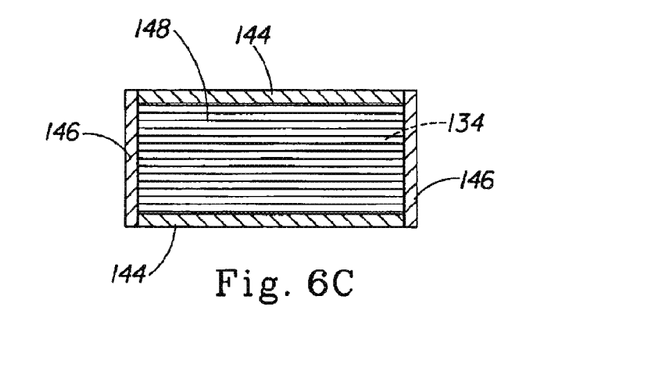
FIG. 6c shows an underlying layer of core wrap material with a plurality of adhesive application patterns from that of FIG. 6.

FIG. 6 shows the absorbent core assembly 130 of FIG. 2a. Said absorbent core assembly is shown in an exploded view represented as FIGS. 7a, 7b, 7c. Accordingly, FIG. 6a shows dusting layer 132 having a central adhesive 142 applied in a striped pattern. While a striped pattern is shown, one skilled in the art would appreciate that other adhesive application patterns may be used. FIG. 6b shows the vacuum-formed outline of a mixture of fluff material 136 and SAP 138. While an hour-glass shape is shown, one skilled in the art would appreciate that other shapes may be used. Lastly, FIG. 6c shows an underlying layer of core wrap material 134 with a plurality of adhesive application patterns, namely, side adhesive 144 and end adhesive 146 applied to the perimeter of said core wrap. Additionally, an auxiliary adhesive 148 may be applied in the field within said side and end adhesives. The use of all of these adhesives helps to form a laminate of said dusting layer, fluff material/SAP and core wrap.

Figure 7:
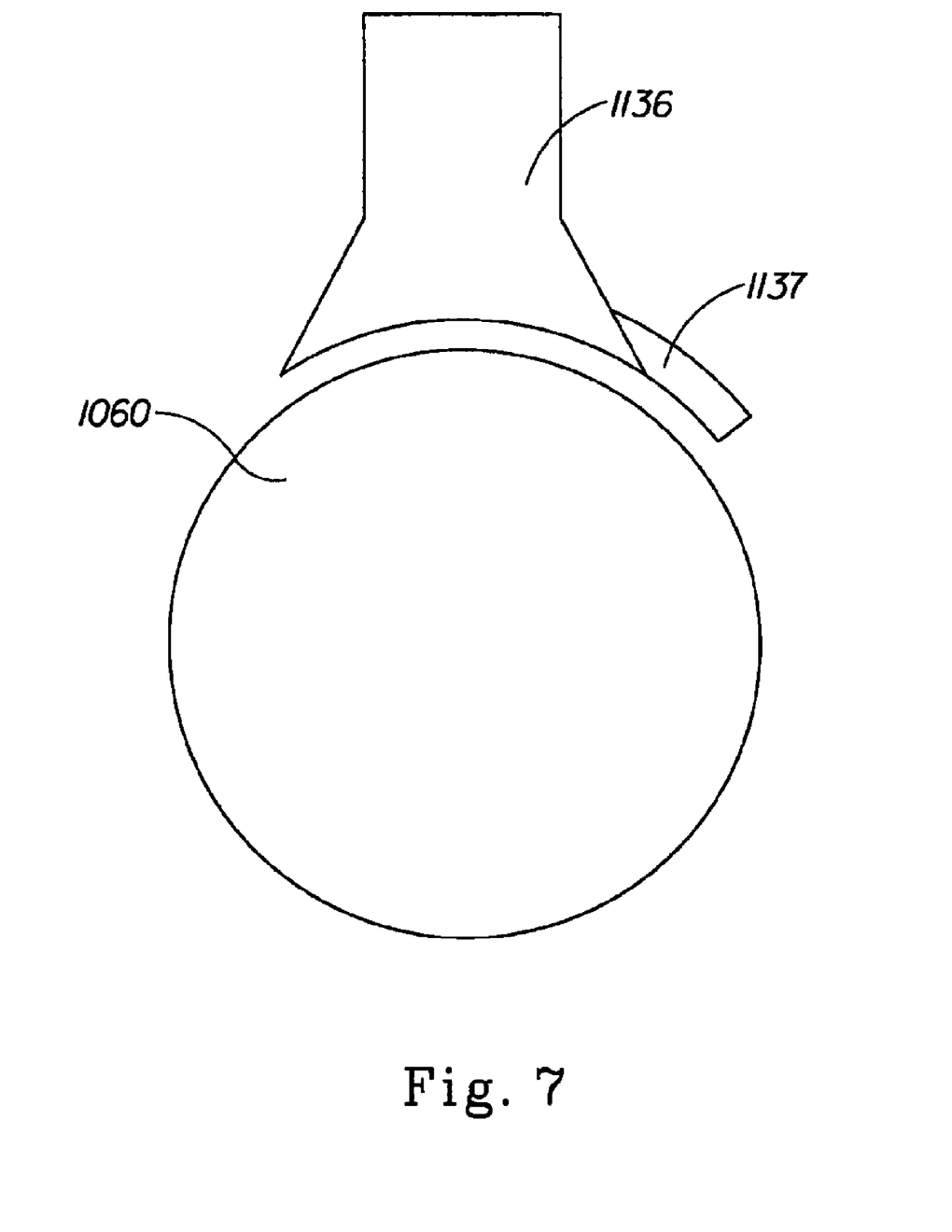
FIG. 7 shows the addition of an SAP shield to the fluff material deposition chute of FIG. 3.

FIG. 7 shows the addition of an SAP shield 1137 which may be attached to said fluff material deposition chute 1136 so as to extend the amount of coverage around said laydown drum 1060 and thus help minimize the amount of SAP particles which might otherwise bounce off of said laydown drum and away from the web.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

For example, while particulate material comprising SAP and fluff material was discussed in the embodiments above, one skilled in the art would appreciate that particulate material containing substantially SAP (e.g., air-felt free) would be within the scope of the present invention. Further, one skilled in the art would appreciate that said particulate material containing substantially SAP may also comprise adhesive. Said adhesive may be mixed with the SAP prior to deposition or directly applied to a material layer.

What is claimed is:

1. An apparatus for forming an absorbent core assembly containing a discrete batt of particulate material comprising:
   a laydown drum comprising a plurality of vacuum zones, said vacuum zones being substantially permeable to permit air to pass through and into said laydown drum, a plurality of fence zones, said fence zones being substantially impermeable to inhibit air from passing through, said fence zones being positioned laterally adjacent to said vacuum zones, and a plurality of blow-off zones, said blow-off zones being substantially permeable to permit air to pass out of and through said laydown drum, said blow-off zones being positioned between said vacuum zones.

2. The apparatus of claim 1 wherein said particulate material comprises superabsorbent polymer and fluff material.

3. The apparatus of claim 1 wherein said particulate material comprises superabsorbent polymer.

4. A method of forming an absorbent core assembly containing a discrete batt of particulate material comprising the steps of:

providing a laydown drum, said laydown drum comprising a plurality of vacuum zones, said vacuum zones being substantially permeable to permit air to pass through and into said laydown drum, a plurality of fence zones, said fence zones being substantially impermeable to inhibit air from passing through, said fence zones being positioned laterally adjacent to said vacuum zones, and a plurality of blow-off zones, said blow-off zones being substantially permeable to permit air to pass out of and through said laydown drum, said blow-off zones being positioned between said vacuum zones;

providing a continuous first web of material;

positioning said continuous first web of material substantially adjacent to said laydown drum;

generating a vacuum through said laydown drum and said continuous first web of material such that air is passed through said vacuum zones;

depositing a dispersion of air and particulate material onto said continuous first web of material such that the air being pulled through the vacuum zones directs said dispersion to said vacuum zones whereupon the particulate material is positioned to form said batt;

blowing air through said blow-off zones so as to substantially displace said particulate material from a position located above said blow-off zones; and severing said continuous web to separate said absorbent core assembly.

5. The method of claim 4, wherein said particulate material comprises superabsorbent polymer and fluff material.

6. The method of claim 4, wherein said particulate material comprises superabsorbent polymer.

7. The method of claim 6, further comprising shielding the deposited superabsorbent polymer particles in order to prevent them from bouncing off of said laydown drum.

* * * * *